(12) United States Patent
Tabata

(10) Patent No.: US 7,715,006 B2
(45) Date of Patent: May 11, 2010

(54) OPTICAL SYSTEM FOR A PARTICLE ANALYZER AND PARTICLE ANALYZER USING SAME

(75) Inventor: Seiichiro Tabata, Sanda (JP)

(73) Assignee: Sysmex Corporation, Kobe (JP)

( * ) Notice: Subject to any disclaimer, the term of this patent is extended or adjusted under 35 U.S.C. 154(b) by 117 days.

(21) Appl. No.: 11/881,323

(22) Filed: Jul. 26, 2007

(65) Prior Publication Data
US 2008/0024758 A1 Jan. 31, 2008

(30) Foreign Application Priority Data
Jul. 31, 2006 (JP) .............................. 2006-209263

(51) Int. Cl.
*G01N 21/00* (2006.01)
*G01N 33/48* (2006.01)
(52) U.S. Cl. ........................ 356/338; 356/336; 356/337; 356/73
(58) Field of Classification Search ......... 356/335–343, 356/39–40, 73, 318; 250/458.1, 459.1, 461.2; 436/63, 173
See application file for complete search history.

(56) References Cited

U.S. PATENT DOCUMENTS

| | | | | |
|---|---|---|---|---|
| 3,724,957 A | * | 4/1973 | Tamate et al. ............... 356/367 |
| 4,577,964 A | | 3/1986 | Hansen, Jr. | |
| 5,185,265 A | * | 2/1993 | Steen et al. .................... 436/63 |
| 5,633,503 A | * | 5/1997 | Kosaka ....................... 250/458.1 |
| 5,731,867 A | * | 3/1998 | Katayama ...................... 356/73 |
| 5,872,627 A | * | 2/1999 | Miers .......................... 356/338 |
| 5,999,256 A | * | 12/1999 | Jones et al. .................. 356/335 |
| 6,215,587 B1 | * | 4/2001 | Alfano et al. ................ 359/368 |
| 6,713,019 B2 | | 3/2004 | Ozasa et al. | |
| 6,794,671 B2 | * | 9/2004 | Nicoli et al. ................. 250/574 |
| 7,060,992 B1 | * | 6/2006 | Barney ....................... 250/458.1 |
| 7,075,647 B2 | * | 7/2006 | Christodoulou ............. 356/339 |

FOREIGN PATENT DOCUMENTS

JP 62025237 A * 2/1987

* cited by examiner

*Primary Examiner*—Sang Nguyen
(74) *Attorney, Agent, or Firm*—Brinks Hofer Gilson & Lione

(57) ABSTRACT

A compact optical system for a particle analyzer and particle analyzer using same are provided. The optical system for a particle analyzer of the present invention comprises a light source, an irradiation optical system for irradiating particles passing through a flow cell with light from the light source, a photodetector for receiving the scattered light from the particles, a light shielding member for blocking the direct light from the light source from impinging the photodetector, and a detecting lens for directing the scattered light toward the photodetector, wherein the irradiation optical system forms a first focus that focuses the light from the light source on the particle passing through the flow cell, and forms a second focus that focuses the light from the light source at a position between the detecting lens and photodetector, and disposes the light shielding member at the position of the second focus.

17 Claims, 14 Drawing Sheets

図1A

図1B (b)

(b)

Scattering characteristic

OPTICAL SYSTEM FOR A PARTICLE ANALYZER AND PARTICLE ANALYZER USING SAME

RELATED APPLICATIONS

This application claims priority under 35 U.S.C. §119 to Japanese Patent Application No. JP2006-209263 filed Jul. 31, 2006, the entire content of which is hereby incorporated by reference.

FIELD OF THE INVENTION

The present invention relates to an optical system for a particle analyzer and a particle analyzer using this optical system.

BACKGROUND

Methods using flow cytometers are generally known as methods for detecting hemocytes in blood and the tangible constituents found in urine and the like.

Flow cytometers analyze particles by irradiating particles flowing in a flow cell, and detecting optical information from the particles.

For example, flow cytometers provided with the optical system shown in FIGS. 1A and 1B are known (U.S. Pat. No. 4,577,964). The optical system shown in FIG. 1A is configured by a laser 101, beam separator 102, photodetector 103, a lens pair 106 including cylindrical lenses 104 and 104, obstacle 113 such as a wire or the like, microscope objective lens 115, opaque screen 117, lens 118, and photodetector 119. FIG. 1B shows the light path of the incident radiation from the laser 101 that has passed through the cylindrical lenses 104 and 105.

Light from the light source laser 101 is focused at points 112 and 114 by the cylindrical lenses 104 and 105. Point 112 is focused on the cells passing through the channel 107. Point 114 is focused on the wire 113. That is, the wire 113 blocks all the light from the lens pair 106 directly through the point 112. Thus, the direct light from the lens pair 106 is blocked by the wire 113. At point 112, the light scattered by the cells (scattered light) passes the wire 113 and reaches the microscope objective lens 115. The scattered light is collected by the positioned in the center of the image plane of the objective lens 115. Therefore, only the scattered light passes through the aperture 116 and reaches the photodetector 119.

In recent years, demand has increased for compact analyzers provided with flow cytometers, for example, blood analyzers. In the optical system of the flow cytometer disclosed in U.S. Pat. No. 4,577,964, a space is required to dispose the light shielding member of the wire 113 between channel 107 of the flow cell and the microscope objective lens 115, which functions as a detecting lens. Therefore, the distance is lengthened between the channel 107 and the microscope objective lens 115. Moreover, a predetermined distance is required between the photodetector 119 and the microscope objective lens 115 to ensure a suitable optical magnification in the photodetector 119. This requirement resulted in problems inasmuch as the longer distance made the detector unit larger, as well as the particle analyzer itself.

SUMMARY

The scope of the present invention is defined solely by the appended claims, and is not affected to any degree by the statements within this summary.

An object of the present invention is to provide an optical system for a particle analyzer that is compact compared to the optical systems used in conventional particle analyzers, and a particle analyzer that uses this compact optical system.

That is, the present invention provides:

(1) an optical system for a particle analyzer comprising a light source, an irradiation optical system for irradiating particles passing through a flow cell, a photodetector for receiving the light from the particles, a light shielding member for blocking the direct light from the light source entering into the photodetector, and a condenser lens for directing the light toward the photodetector, wherein the irradiation optical system forms a first focus that focuses the light from the light source on the particle passing through the flow cell, and forms a second focus that focuses the light from the light source at a position between the condenser lens and photodetector, and disposes the light shielding member at the position of the second focus;

(2) the optical system for the particle analyzer of (1) or (2), wherein the irradiation optical system forms a third focus focusing light from the light source at a position between the flow cell and the light source, and forms the second focus by imaging the third focus using the condenser lens;

(3) the optical system for the particle analyzer of (1), wherein the irradiation optical system forms the first focus of the light from the light source that converges in a parallel direction relative to a direction of passage of the particles and extends in a perpendicular direction relative to the direction of passage of the particles, and forms the second focus that converges in a direction perpendicular to the direction of passage of particles and extends in a parallel direction relative to the direction of passage of particles;

(4) the optical system for the particle analyzer of (2), wherein the irradiation optical system forms the first focus of the light from the light source that converges in a direction parallel to a direction of passage of particles and extends in a perpendicular direction relative to the direction of passage of particles, and forms the third focus that converges in the perpendicular direction relative to the direction of passage of the particles and extends in the parallel direction relative to the direction of passage of the particles;

(5) the optical system for the particle analyzer of any one among (1) through (4), wherein the irradiation optical system has at least one cylindrical lens;

(6) the optical system for the particle analyzer of any one among (1) through (5), further comprising a beam splitter disposed between the detecting lens and the light shielding member, a second photodetector for receiving part of the light split by the beam splitter, and a second light shielding member disposed between the beam splitter and the second photodetector;

(7) the optical system for a particle analyzer of (6), wherein the light shielding member having a different scattering angle range for the transmitted light is disposed relative to the light path split by the beam splitter;

(8) the optical system for a particle analyzer of any among (1) through (5) have a dichroic mirror disposed between the detecting lens and the light shielding member, and have a fluorescence detector for receiving fluorescent light split by the dichroic mirror;

(9) a particle analyzer comprising a flow cell through which particles pass, a light source, an irradiation optical system for irradiating the particles passing through a flow cell, a photodetector for receiving the light from the particles, a light shielding member for blocking the direct light from the light source entering into the photodetector, a detecting lens for directing the light from the particles toward the photodetector, and an analyzing part for analyzing particles based on detection signals detected by the photodetector, wherein the irradiation optical system forms a first focus that focuses the light from the light source on the particle passing through the flow cell, and forms a second focus that focuses the light from the light source at a position between the detecting lens and photodetector, and the photoreceiving optical system provides a light shielding member at the position of the second focus;

(10) the particle analyzer of (9), wherein the irradiation optical system forms a third focus focusing light from the light source at a position between the flow cell and the light source, and forms the second focus by imaging the third focus using the detecting lens;

(11) the particle analyzer of any one among (9) and (10), wherein the irradiation optical system forms the first focus that converges the light from the light source in a direction parallel to the direction of passage of the particles, and extends in a perpendicular direction relative to the direction of passage of the particles, and the second focus that converges the light from the light source in the direction perpendicular to the direction of passage of the particles, and extends in the parallel direction relative to the direction of passage of the particles; and

(12) the particle analyzer of (10), wherein the irradiation optical system forms the first focus of the light from the light source that converges in a direction parallel to the direction of passage of particles and extends in a perpendicular direction relative to the direction of passage of particles, and forms the third focus that converges in the perpendicular direction relative to the direction of passage of the particles and extends in the parallel direction relative to the direction of passage of the particles.

The present invention provides a compact optical system for a particle analyzer and particle analyzer using same. The present invention realizes a compact optical system that does not increase cost or complexity of the mechanism.

DETAILED DESCRIPTION OF THE EMBODIMENT

Figure 1:
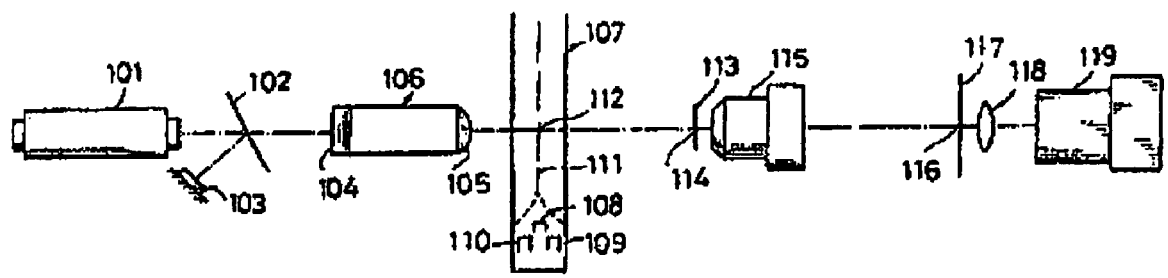
FIG. 1 briefly shows an optical system in a conventional flow cytometer.
Figure 1:
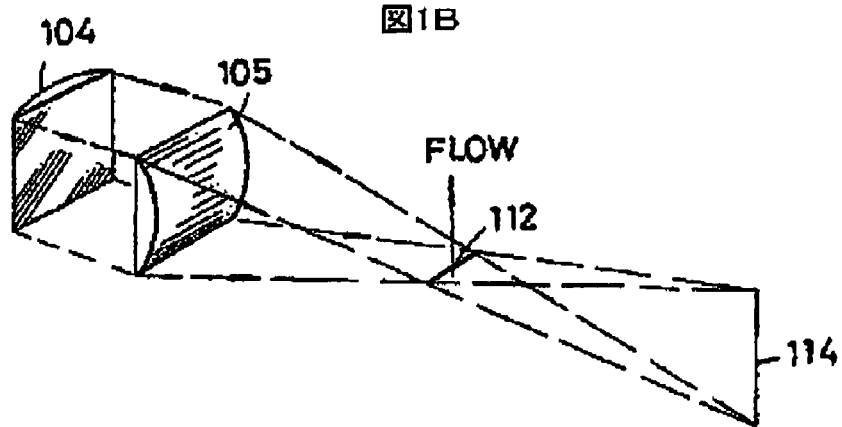
Figure 2:
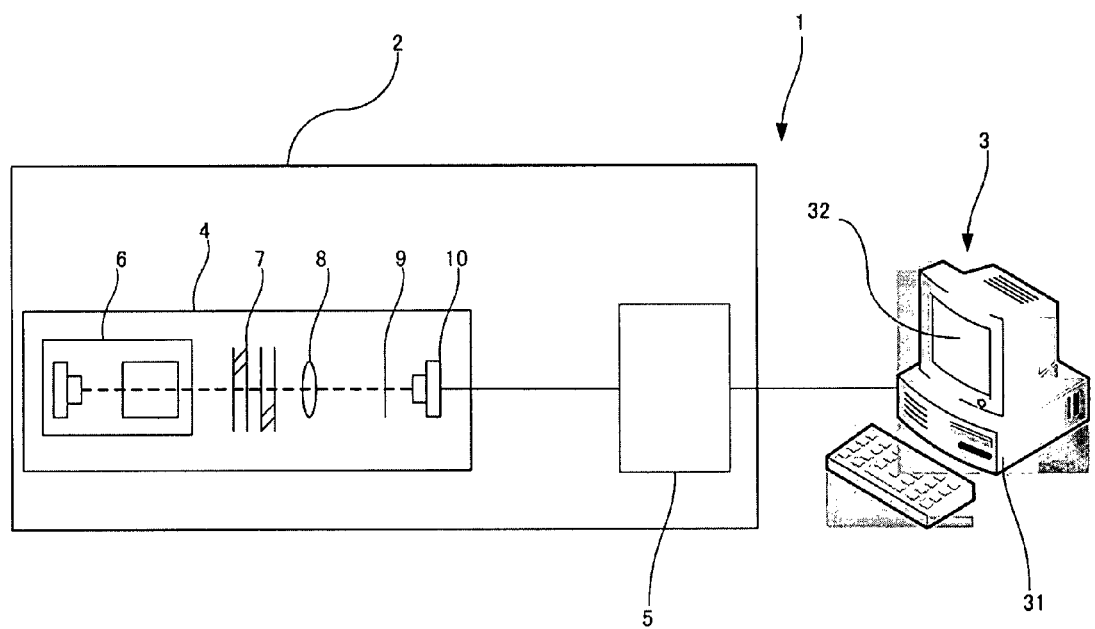
FIG. 2 briefly shows the structure of a particle analyzer.

FIG. 2 shows an embodiment of the structure of the particle analyzer of the present invention. The particle analyzer 1 of FIG. 2 is configured by a measuring unit 2 and analyzing unit 3. The measuring unit 2 includes a detection part 4 and controller 5. The detection part 4 is provided with a flow cell, an irradiation optical system 6 for irradiating particles passing through the flow cell 7 with laser light, a detecting lens 8 for guiding the scattered light from the particles toward a photodiode 10, a light shielding plate 9 for blocking the direction light from the irradiation optical system 6, and a photodiode 10 for receiving the scattered light from the particles. The controller 5 transmits the light signals detected by the photodiode 10 as digital signals to an information processing unit 31 of the analyzing part 3. The information processing unit 31 of the analyzing part 3 processes and analyzes the digital signals which reflect the characteristics of the particles. The processing and analysis results obtained by the information processing unit 31 are displayed on an output unit 32. A first embodiment of the optical system for a particle analyzer of the present invention is described hereinafter using FIGS. 3 and 4.

Figure 3:
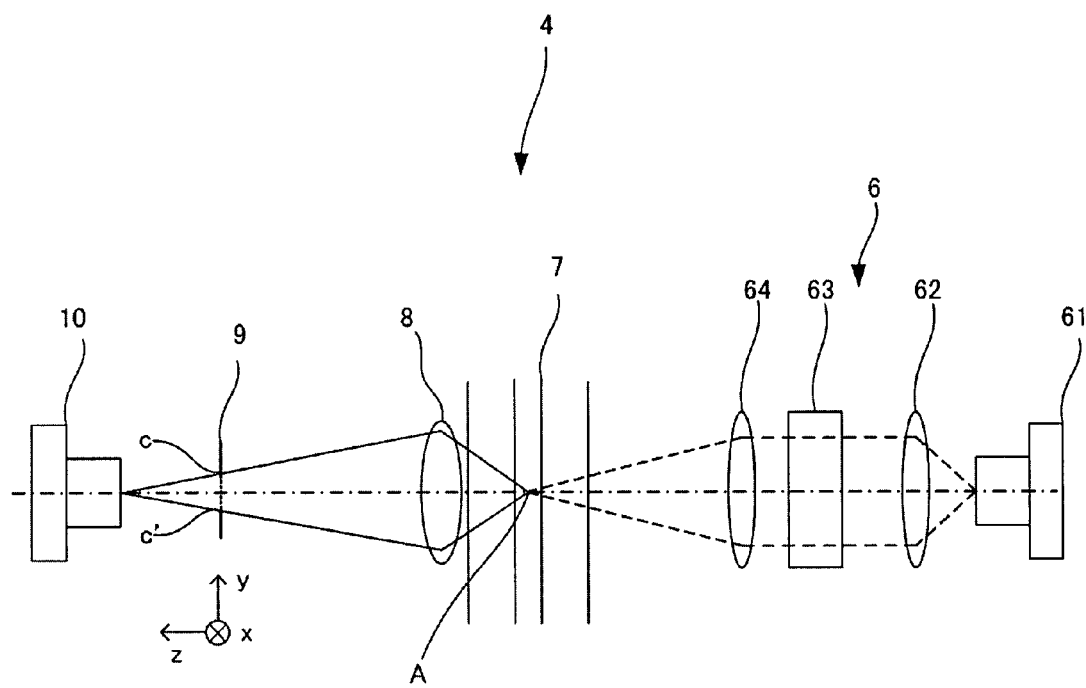
FIG. 3 is a side view of the detection part provided with a first embodiment of the optical system of the particle analyzer of the present invention.
Figure 4:
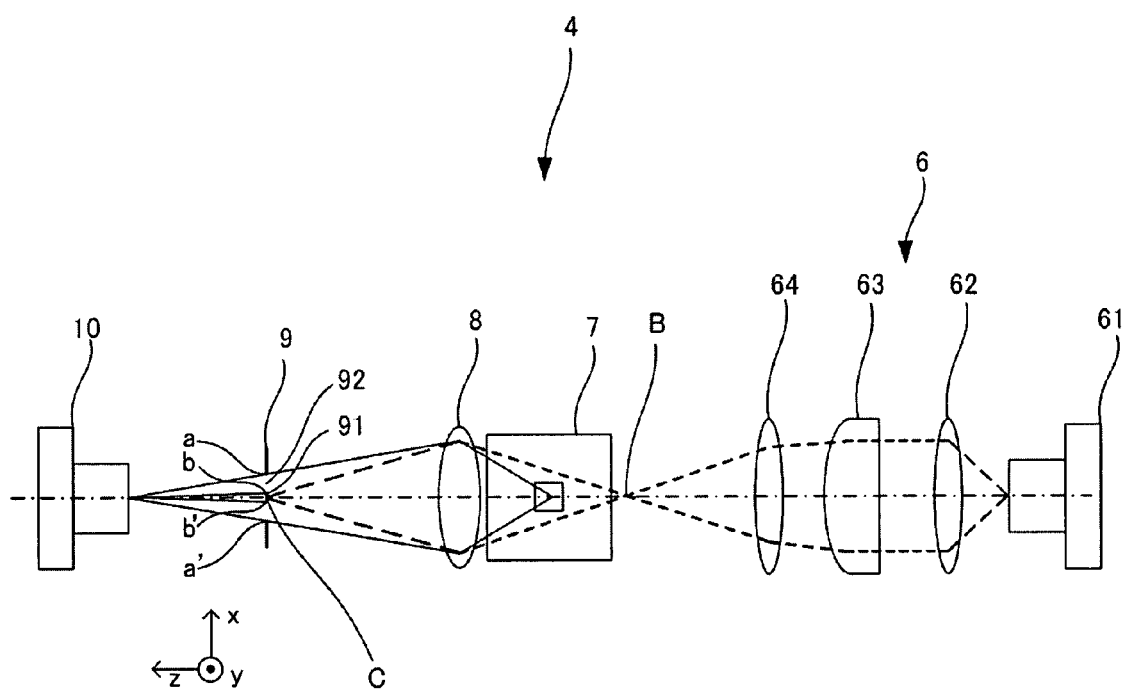
FIG. 4 is a top view of the detection part provided with a first embodiment of the optical system for a particle analyzer of the present invention.

FIG. 3 is a side view, and FIG. 4 is a top view (viewed from the top of the diagram of FIG. 3) of the detection part 4. The detection part 4 shown in FIGS. 3 and 4 is configured by an irradiation optical system 6, flow cell 7 provided with a channel in which particles flow in the y direction, photodiode 10 for receiving scattered light from the particles, spherical detecting lens 8 for focusing the scattered light from the particles on the photodiode 10, and light shielding plate 9 for blocking the direct light which passes through the flow cell 7.

The irradiation optical system 6 is provided with a laser diode 61 as a light source, collimator lens 62 for converting the laser light emitted from the laser diode 61 to parallel rays, convex cylindrical lens 63 for focusing the light impinging the collimator lens 62 in a horizontal direction (direction perpendicular to the flow of the flow cell), and spherical condenser lens 64 for focusing the light from the convex cylindrical lens 63 on the flow cell 7.

In FIGS. 3 and 4, the light path of the direct light emitted from the laser diode 61 is indicated by dashed lines. The light path of the scattered light from the particles flowing in the flow cell 7 is indicated by solid lines.

Also in FIGS. 3 and 4, the z direction is a direction parallel to the optical axis of the laser light. The y direction is perpendicular to the z direction, and is parallel to the channel of the particles passing through the flow cell 7. The x direction is perpendicular to both the z direction and y direction. The y direction is referred to the perpendicular direction, and the x direction is referred to as the horizontal direction hereinafter as viewed from the laser diode 61 side.

When viewing the detection part 4 from the side (refer to FIG. 3), the radial laser light emitted from the laser diode 61 is converted to parallel rays by the collimator lens 62. These parallel rays are not refracted as they pass through the convex cylindrical lens 63. Then, the parallel rays that have passed through the convex cylindrical lens 63 are focused at a first focusing point A in the center of the particle flow of the flow cell 7 by the condenser lens 64. The first focusing point A is positioned at or near the focus of the condenser lens 64. The beam at the first focusing point A is hyperelliptic in shape (the shape of the beam viewed from the laser diode 61 side), converging in the perpendicular direction (y direction) and extending in the horizontal direction (x direction). The direct light that has passed through the first focusing point A is masked by the light shielding plate 9. However, the scattered light from the particles is focused by the detecting lens 8 and impinges the photodiode 10.

When viewing the detection part 4 from above (refer to FIG. 4), the radial laser light emitted from the laser diode 61 is converted to parallel rays by the collimator lens 62. These parallel rays are focused at a second focusing point B in front of the flow cell 7 by the convex cylindrical lens 63 and condenser lens 64. The beam at the second focusing point B is hyperelliptic in shape (the shape of the beam viewed from the laser diode 61 side), converging in the horizontal direction (x direction) and extending in the perpendicular direction (y direction). The laser light that has passed through the second focusing point B is focused at a third focusing point C by the detecting lens 8. The beam at the third focusing point C is hyperelliptic in shape (the shape of the beam viewed from the laser diode 61 side), converging in the horizontal direction (x direction) and extending in the perpendicular direction (y direction).

Figure 5:
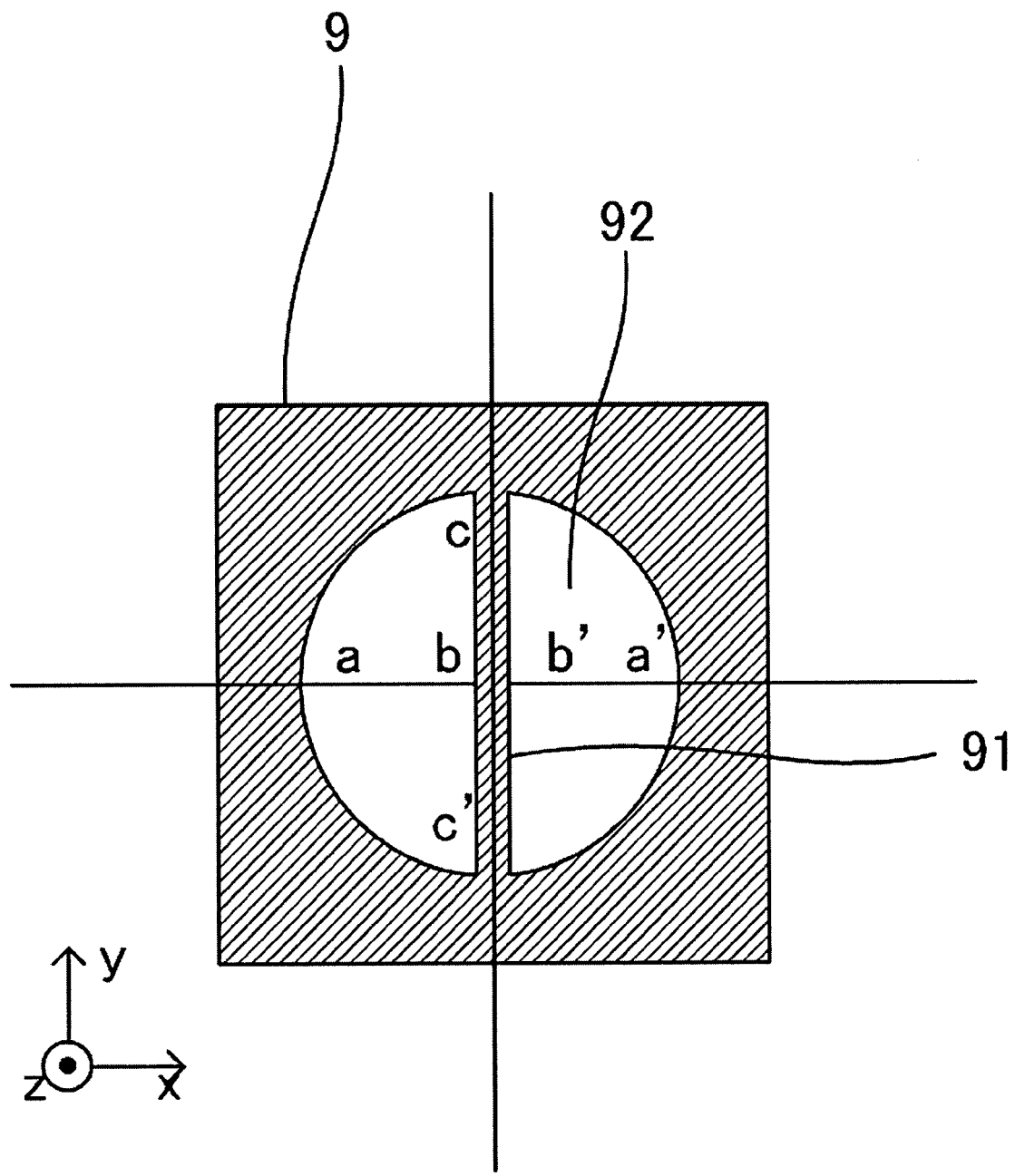
FIG. 5 shows a light shielding plate.

The light shielding plate 9 is positioned at the third focusing point C. As shown in FIG. 5, the light shielding plate 9 has a circular aperture 92 formed in the center part, and is provided with a wire-like light shielding part 91 in the center of the circular aperture 92. The light shielding part 91 vertically sections the circular aperture 92 by extending in the perpendicular direction (y direction), and has a narrow width in the horizontal direction (x direction). As previously mentioned, the beam at the third focusing point C is hyperelliptic in shape, converging in the horizontal direction (x direction) and extending in the perpendicular direction (y direction). Therefore, the laser light (direct light) is completely blocked by the light shielding part 91. The scattered light from the particles at the first focusing point A is focused by the detecting lens 8, and impinges the photodiode 10 through the circular aperture 92 of the light shielding plate 9.

In FIG. 5, the maximum scattering angle at which the photodiode 10 receives light is defined by the length of the diameter a-a' of the circular aperture 92 of the light shielding plate 9. Moreover, the minimum scattering angle at which the photodiode 10 receives light is defined by the length of the width b-b' of the wire-like light shielding part 91. Therefore, a light shielding plate may be used which has a suitable a-a' value and b-b' value for the object being measured. The light shielding plate 9 can be easily formed by processing a metal plate or the like coated with a black color.

The present invention does not require that the light shielding plate 9 is disposed between the flow cell 7 and the detecting lens 8. Therefore, the distance between the flow cell 7 and the detecting lens 8 can be shortened.

For example, in the conventional art, when scattered light from particles is received by the photodiode 10 at an optical magnification of 20-fold using a detecting lens 8 with a focal length of approximately 8 mm, the photodiode 10 must be positioned a distance of 160 mm from the detecting lens 8. In the present embodiment, however, space is not required for the light shielding plate 9. Thus, when scattered light from particles is received by the photodiode 10 at an optical magnification of 20-fold using a detecting lens 8 with a focal length of approximately 4 mm, the photodiode 10 may be positioned a distance of 80 mm from the detecting lens 8. Therefore, the optical system is rendered substantially more compact.

Figure 6:
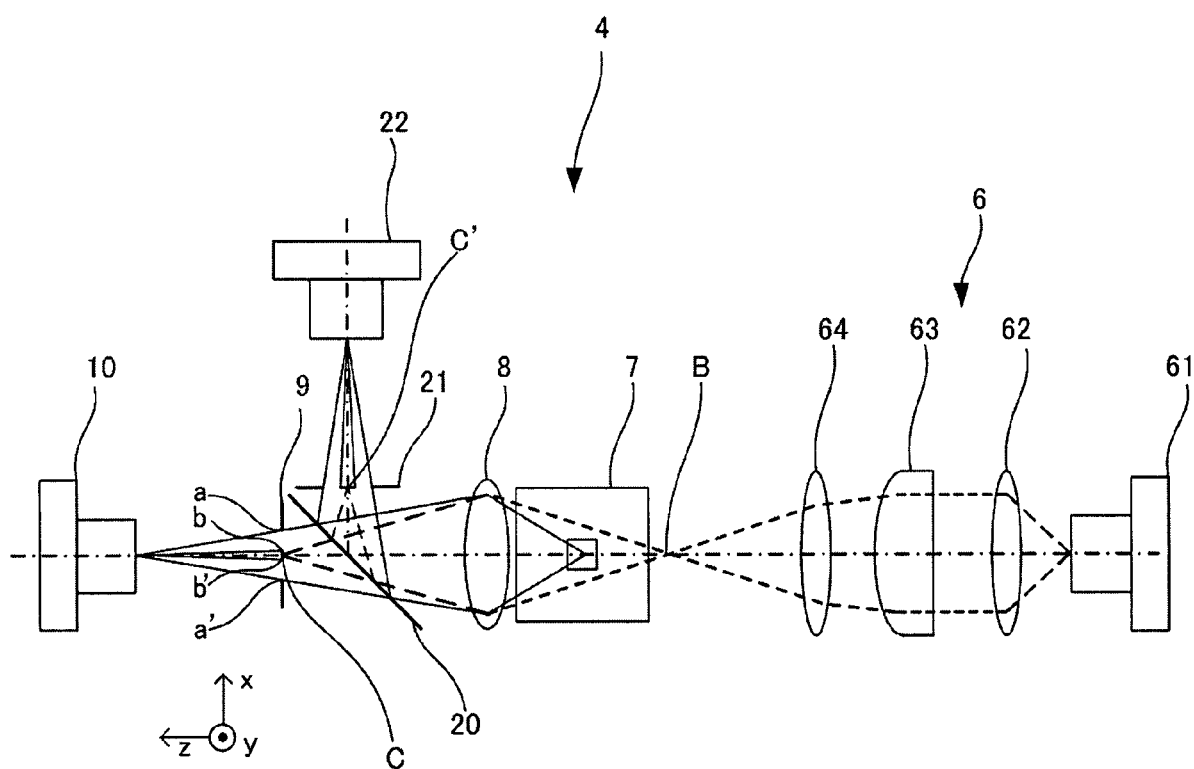
FIG. 6 is a top view of the detection part provided with a second embodiment of the optical system of the particle analyzer of the present invention.

FIG. 6 is a top view of the detection part 4 provided with a second embodiment of the optical system of the present invention. Parts of the structure in common with the first embodiment are identified by the same reference numbers. The second embodiment of the optical system for a particle analyzer is configured by an irradiation optical system 6, detecting lens 8, beam splitter 20, light shielding plate 9 disposed in the light path of the light transmitted by the beam splitter 20, photodiode 10, light shielding plate 21 disposed in the light path of the light reflected by the beam splitter 20, and photodiode 22. The light path of the scattered light from the particles flowing through the flow cell 7 is indicated by a solid line. The path of the direct light from the laser diode 61 is indicated by a dashed line.

The light transmitted by the beam splitter 20 follows the same light path as the first embodiment. That is, the direct light from the laser diode 61 becomes a hyperelliptic beam converging in the horizontal direction (x direction) and extending in the perpendicular direction (y direction) at the third focusing point C at the position of the light shielding plate 9. Therefore, this direct light is blocked by the light shielding part 91 of the light shielding plate 9. The scattered light from the particles passes through the circular aperture 92 of the light shielding plate 9, and impinges the photodiode 10.

However, the direct light from the laser diode 61 reflected by the beam splitter 20 becomes a hyperelliptic beam extending in the perpendicular direction (y direction) similar to the third focusing point C at the third focusing point C' at the position of the light shielding plate 21. Therefore, the direct light is blocked by the light shielding part 211 of the light shielding plate 21 shown in FIG. 7. The scattered light from the particles passes through the circular aperture 212 of the light shielding plate 21, and impinges the photodiode 22.

Figure 7:
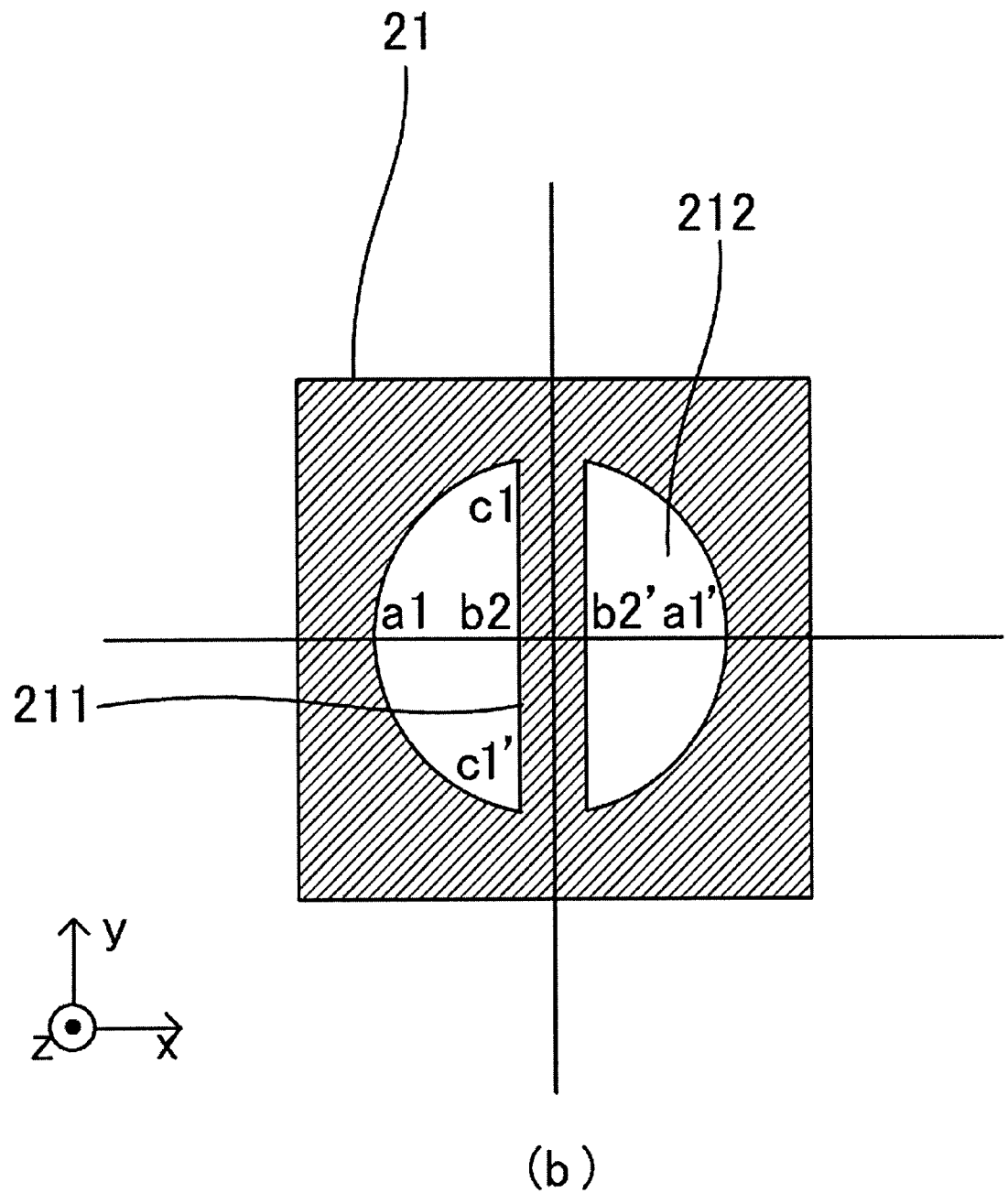
FIG. 7 shows a light shielding plate in which the light shielding part has a different width.

The light shielding plate 21 shown in FIG. 7 is provided with a light shielding part 211 that is wider in width than the light shielding part 91 of the light shielding plate 9 shown in FIG. 5. The minimum scattering angle of the scattered light passing through the circular aperture 212 of the light shielding plate 21 is greater than the minimum scattering angle of the scattered light passing through the circular aperture 91 of the light shielding plate 9. As a result, the photodiode 22 receives scattered light from a greater minimum scattering angle than the photodiode 10.

Figure 8:
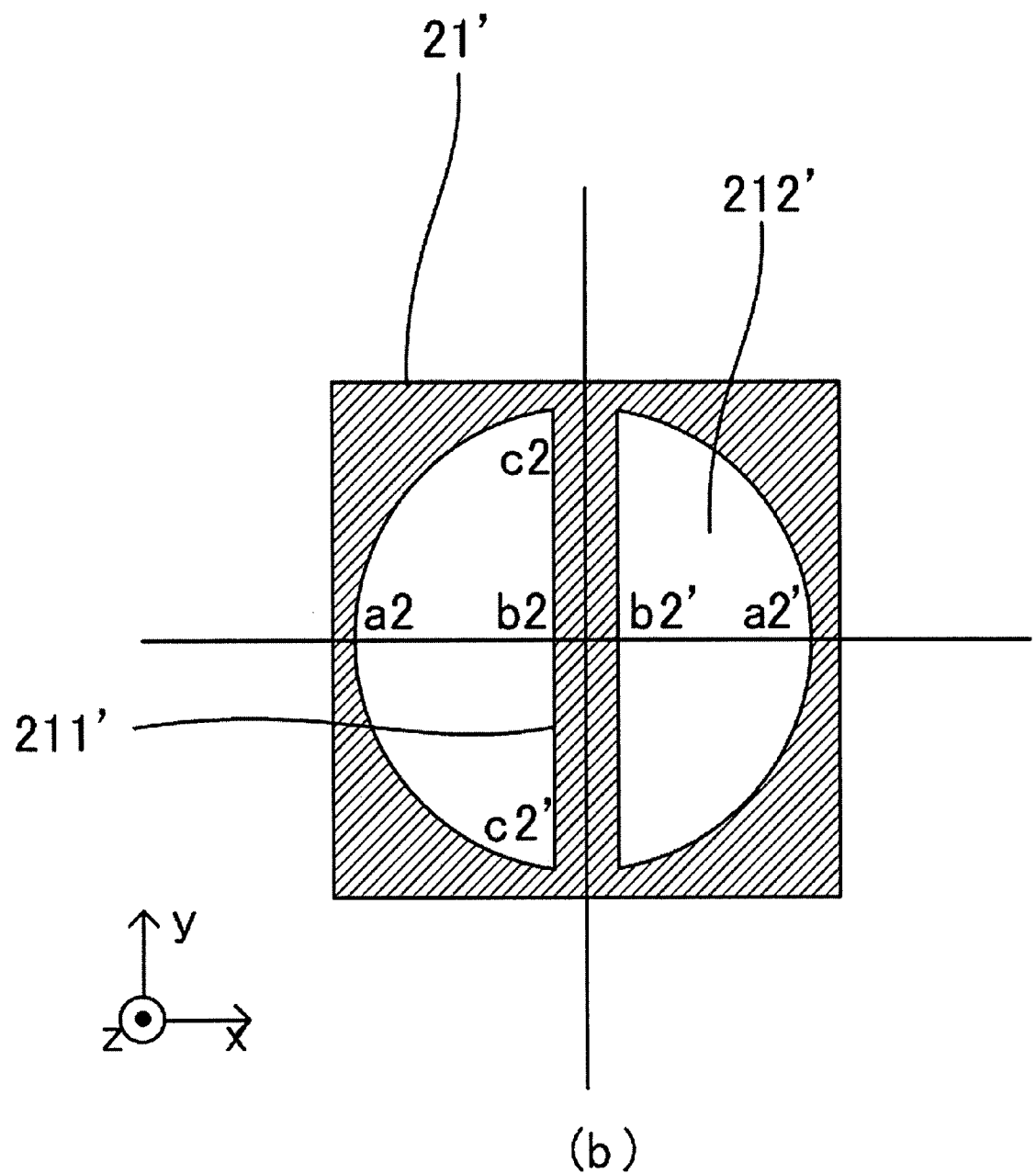
FIG. 8 shows a light shielding plate in which the width of the light shielding part and the diameter of the circular aperture are different.

A modification of the light shielding plate is shown in FIG. 8. The light shielding plate 21' is provided with a light shielding part 211' that is wider in width than the light shielding part 91 of the light shielding plate 9, and a circular aperture 212' that has a larger diameter than the circular aperture 92. Therefore, the minimum scattering angle and maximum scattering angle of the scattered light passing through the circular aperture 212' are greater than the minimum scattering angle and maximum scattering angle of the scattered light passing through the circular aperture 92. As a result, the photodiode 22 receives scattered light from both a larger minimum scattering angle and larger maximum scattering angle than the photodiode 10.

Figure 9:
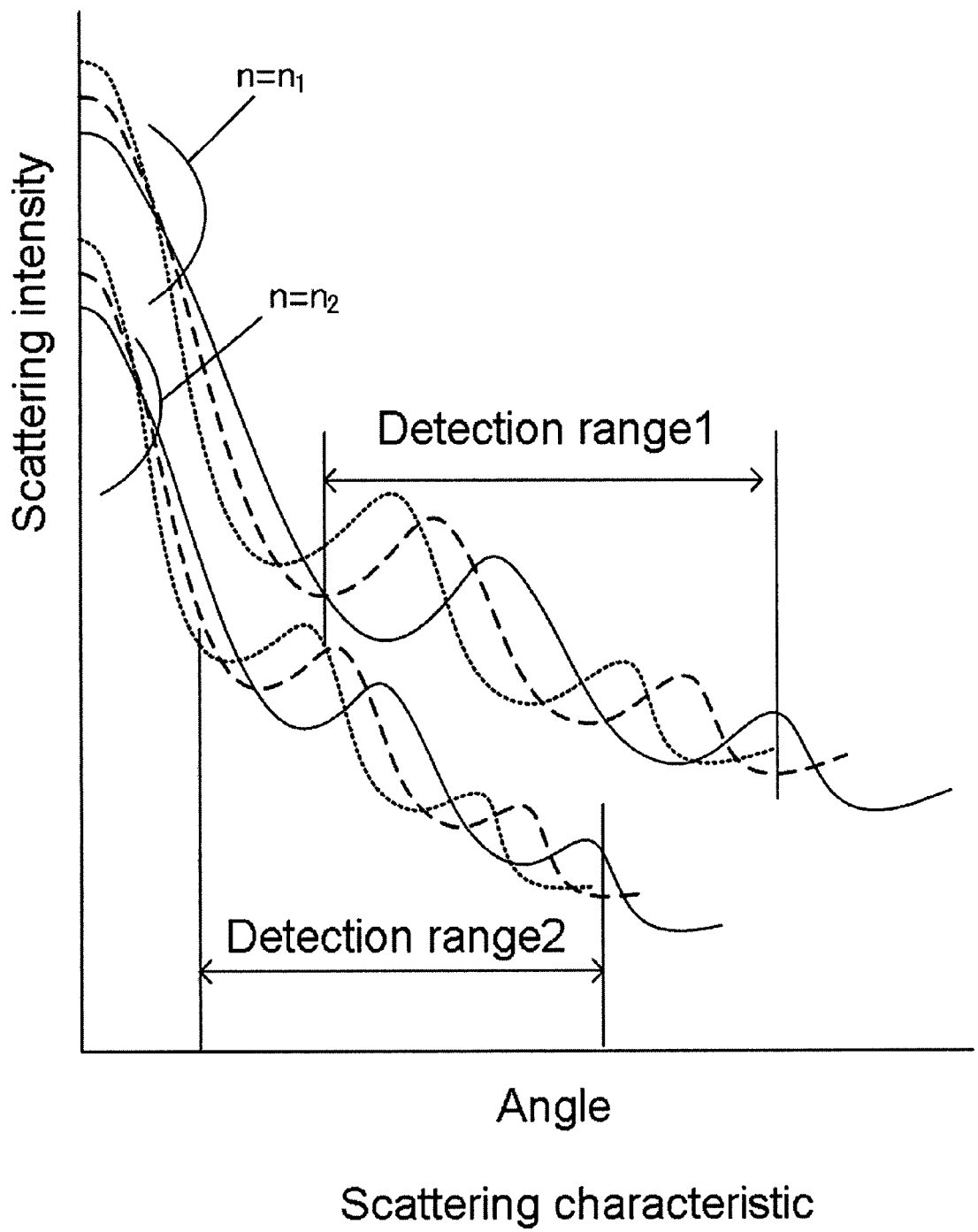
FIG. 9 shows the scattering angle characteristics related to scattered light intensity and angle.

A schematic drawing of the angle distribution of scattering characteristics is shown in FIG. 9 to illustrate the scattering angles. The optimum scattering angle range differs depending on the size and refractive index of the particle. When the refractive index n is different at n1 and n2, the scattering characteristics change depending on the size of the particle.

Therefore, the detection range also changes to readily reflect the size of the particle. Samples that include a plurality of particles types having different scattering characteristics can be measured using an optical system capable of detecting scattered light at different scattering angles, as in the second embodiment shown in FIG. 6.

The second embodiment is capable of easily detecting scattered light having different scattering characteristics by respectively disposing light shielding plate 9 and light shielding plate 21, which have different scattering angle ranges for transmission light, at the third focusing points C and C' in the light path separated by the beam splitter 20.

When a two-dimensional distribution diagram is created based on the signal values of scattered light at different detectable scattering angles detected by the photodiodes 10 and 22, the distribution may also be prepared with a dual axis for the signals values of the photodiode 10 and signal values for the photodiode 22. A dual axis distribution diagram using the signals values of the photodiodes 10 and 22 is effective for illustrating the distribution hemoglobin content and volume in erythrocytes.

Figure 10:
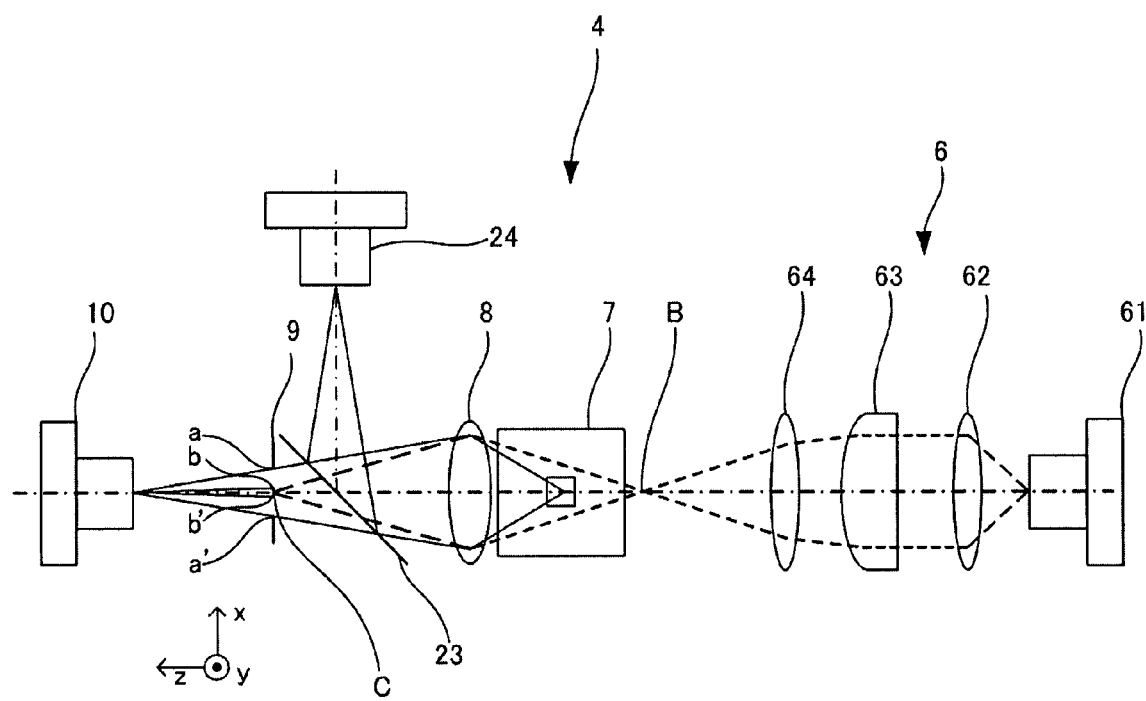
FIG. 10 is a top view of the detection part provided with a third embodiment of the optical system of the particle analyzer of the present invention.

FIG. 10 is a top view of the detection part 4 provided with a third embodiment of the optical system of the particle analyzer. Parts of the structure in common with the previous embodiments are identified by the same reference numbers. The third embodiment of the optical system for a particle analyzer includes a dichroic mirror 23 and photomultiplier 24 added to the first embodiment of the optical system for a particle analyzer. The light path of the scattered light from the particles flowing through the flow cell 7 is indicated by a solid line. The path of the direct light from the laser diode 61 is indicated by a dashed line.

The dichroic mirror 23 has optical characteristics such that the light near the wavelength (approximately 635 nm) is the laser might emitted from the laser diode 61 is allowed to pass through, and light of longer wavelength than the laser light is reflected. That is, the long wavelength fluorescent light from the particles is reflected by the dichroic mirror 23. However, the direct light from the laser diode 61 passes through the dichroic mirror 23. Therefore, there is no need to place a light shielding member between the dichroic mirror 23 and the photomultiplier 24 to block the direct light from the laser diode 61. The direct light transmitted through the dichroic mirror 23 is, however, blocked by the light shielding part 91 of the light shielding plate 9 just as in the first embodiment. The scattered light from the particles passes through the circular aperture 92 of the light shielding plate 9, and impinges the photodiode 10.

In the third embodiment, the forward fluorescent light can be detected by the photomultiplier 24 without mediation by the light shielding plate. Therefore, a reduction of fluorescent light intensity caused by the light shielding plate is prevented. As a result, there is no need for lenses and the like to focus the forward fluorescent light from the particles, unlike when detecting forward fluorescent light. The optical system can thus be rendered even more compact.

Figure 11:
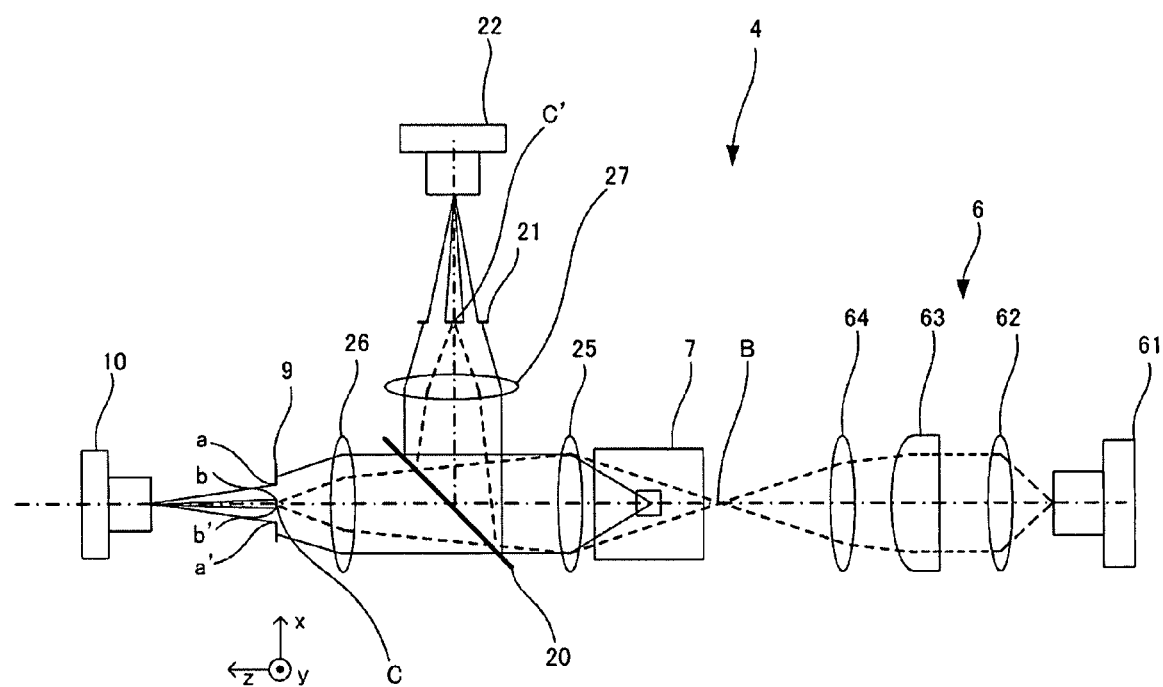
FIG. 11 is a top view of the detection part provided with a fourth embodiment of the optical system of the particle analyzer of the present invention.

FIG. 11 is a top view of the detection part 4 provided with a fourth embodiment of the optical system of the particle analyzer. Parts of the structure in common with the previous embodiments are identified by the same reference numbers. The fourth embodiment of the optical system for a particle analyzer is configured by a collimator lens 25 for converting the scattered light from the particles passing through the flow cell 7 to parallel rays, a beam splitter 20, a first detecting lens 26 disposed in the light path of the light transmitted through the beam splitter 20, light shielding plate 9, photodiode 10, second detecting lens 27 disposed in the light path of the light reflected by the beam splitter 20, light shielding plate 21, and photodiode 22. The light path of the scattered light from the particles flowing through the flow cell 7 is indicated by a solid line. The path of the direct light from the laser diode 61 is indicated by a dashed line.

The direct light from the laser diode 61 passes through the collimator lens 25 and impinges the beam splitter 20. The direct light transmitted through the beam splitter 20 is focused on the third focusing point C at the position of the light shielding plate 9 by the first detecting lens 26. The direct light focused on the third focusing point C is blocked by the light shielding part 91 of the light shielding plate 9. The scattered light from the particles passes through the collimator lens 25 and impinges the beam splitter 20. The scattered light transmitted through the beam splitter 20 passes through the circular aperture 92 of the light shielding plate 9, and impinges the photodiode 10. However, the direct light reflected by the beam splitter 20 is focused on the third focusing point C' at the position of the light shielding plate 21 by the second detecting lens 27. The direct light focused on the third focusing point C' is blocked by the light shielding part 211 of the light shielding plate 21. The scattered light from the particles passes through the circular aperture 212 of the light shielding plate 21, and impinges the photodiode 22.

In the fourth embodiment, the scattered light from the particles that have passed through the flow cell 7 are once rendered parallel rays by the collimator lens 25. Therefore, the position of the first detecting lens 26 which directs the parallel rays to the photodiode 10 can be freely moved on the optical axis of the laser diode 61. That is, the distance from the collimator lens 25 to the first detecting lens 26 can be freely set. Hence, it is possible to ensure adequate space for the disposition of the beam splitter 20 and/or the dichroic mirror 23. A plurality of beam splitters 20 can therefore be disposed to detect scattered light from three or more detectable scattering angles. Moreover, fluorescent light detection can be performed in parallel by positioning the dichroic mirror 23 instead of a beam splitter 20.

Although the embodiment is illustrated using a single beam splitter 20 in FIG. 11, the present invention is naturally not limited to deploying a single beam splitter. As described above, it is possible to deploy a plurality of beam splitters 20 and/or the dichroic mirrors 23.

Figure 12:
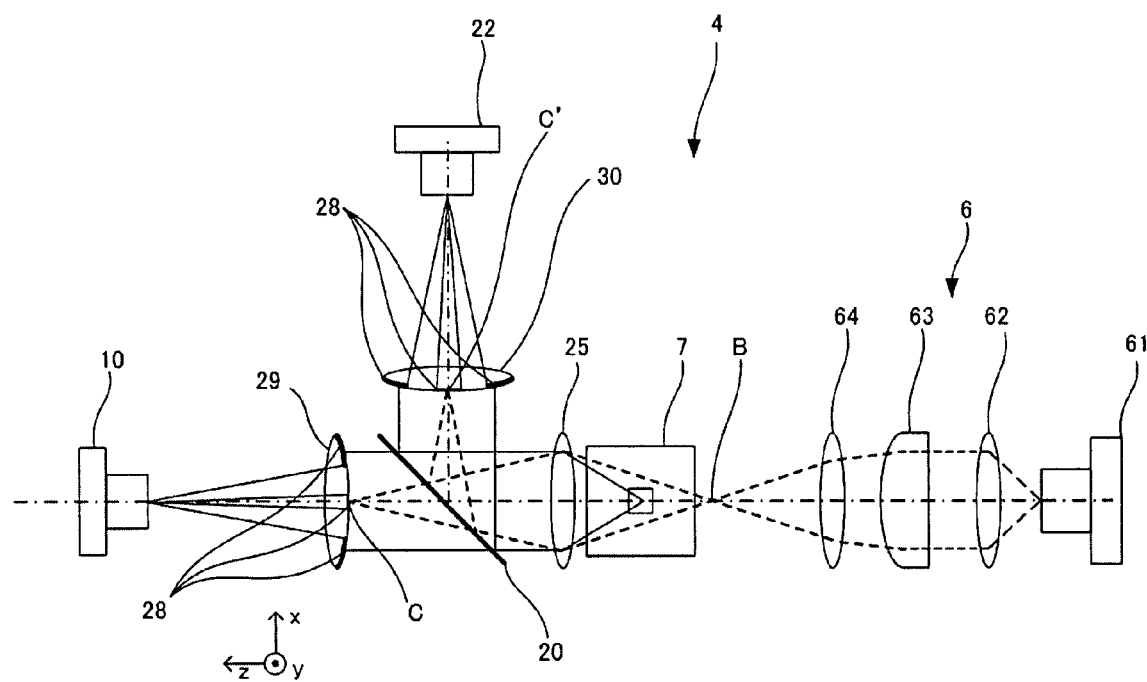
FIG. 12 is a top view of the detection part provided with a fifth embodiment of the optical system of the particle analyzer of the present invention.

FIG. 12 is a top view of the detection part 4 provided with a fifth embodiment of the optical system of the particle analyzer. Parts of the structure in common with the previous embodiments are identified by the same reference numbers. The configuration of the fifth embodiment of the optical system for a particle analyzer is a modification in that the light shielding plate 9 and first detecting lens 26 of the fourth embodiment are changed to a third detecting lens 29 having a black coating 28. The light shielding plate 21 and second detecting lens 27 are also changed to a fourth detecting lens 30 having a black coating 28. The light shielding member and detecting lens are integrated in a single unit. Therefore, the optical axis is easily adjustable.

Figure 13:
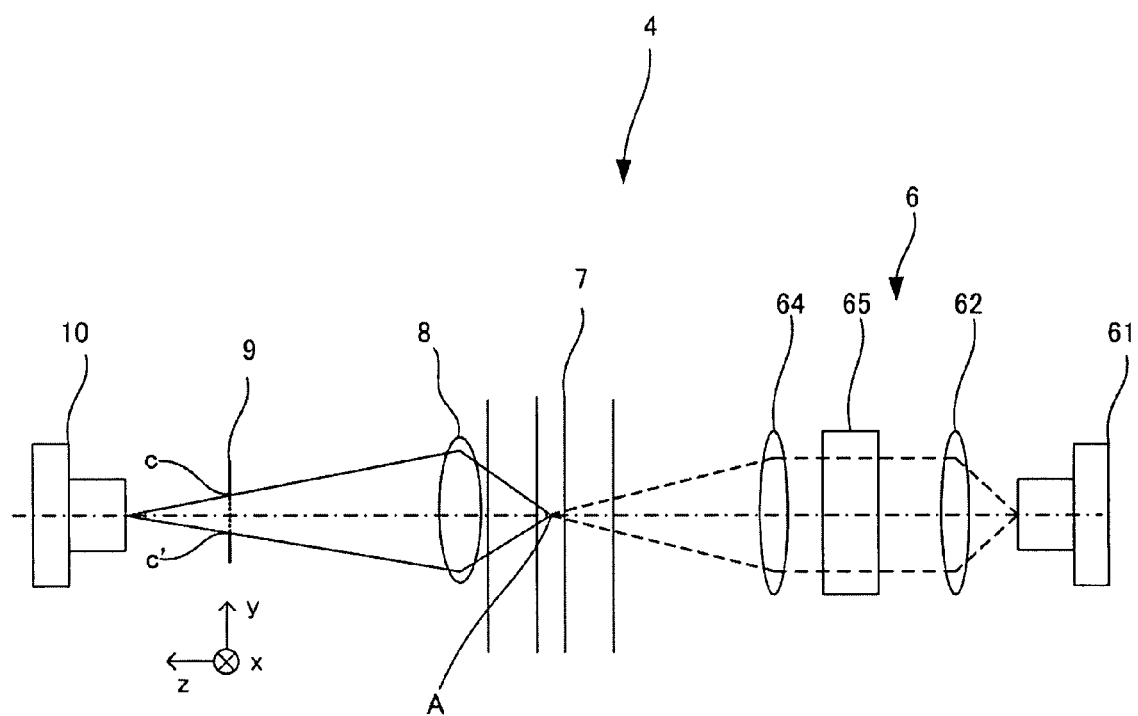
FIG. 13 is a side view of the detection part provided with a sixth embodiment of the optical system of the particle analyzer of the present invention.
Figure 14:
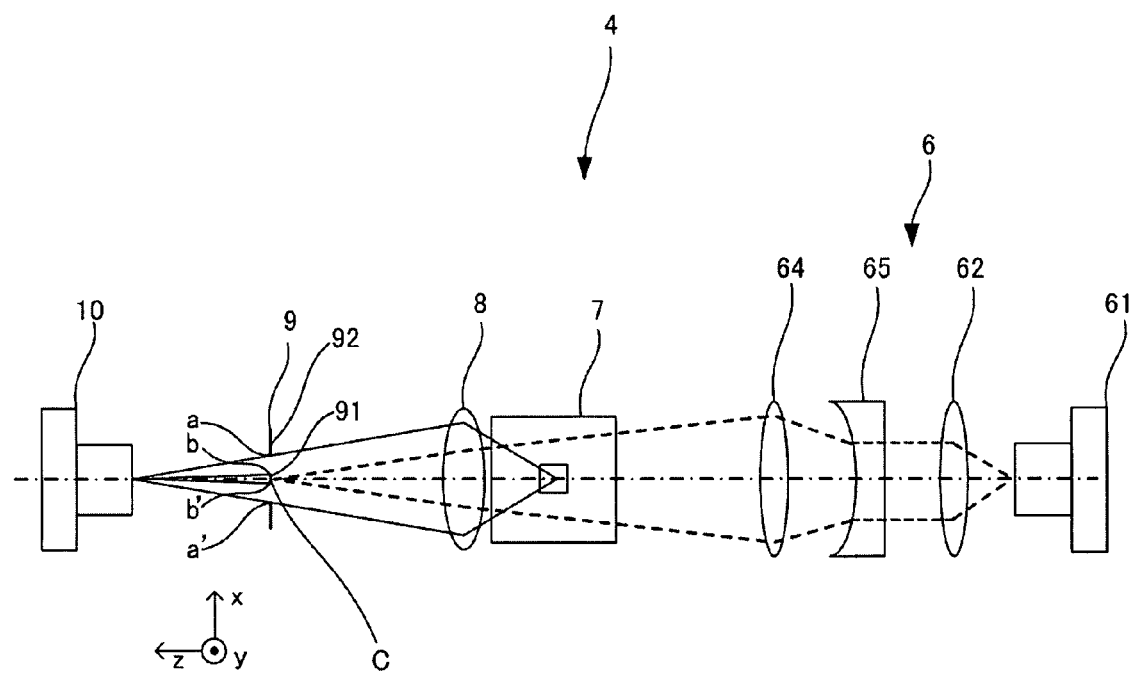
FIG. 14 is a top view of the detection part provided with a sixth embodiment of the optical system of the particle analyzer of the present invention.

FIGS. 13 and 14 illustrate a sixth embodiment of the optical system for a particle analyzer. Parts of the structure in common with the first embodiment are identified by the same reference numbers. The sixth embodiment of the optical system for a particle analyzer is a modification in which the convex cylindrical lens 63 of the irradiation optical system of the first embodiment is changed to a concave cylindrical lens 65. FIG. 13 is a side view of the detection part 4, and FIG. 14 is a top view (viewed from the top of the diagram) of the detection part 4.

When viewing the detection part 4 from the side (refer to FIG. 13), the radial laser light emitted from the laser diode 61 is converted to parallel rays by the collimator lens 62. These parallel rays are not refracted as they pass through the concave cylindrical lens 65. The parallel rays that have passed through the concave cylindrical lens 65 are focused at a first focusing point A in the center of the particle flow of the flow cell 7 by the detecting lens 64. The direct light that has passed through the first focusing point A is masked by the light shielding plate 9. However, the scattered light from the particles is focused by the detecting lens 8 and impinges the photodiode 10.

When viewing the detection part 4 from above (refer to FIG. 14), the radial laser light emitted from the laser diode 61 is converted to parallel rays by the collimator lens 62. These parallel rays are refracted in a horizontal direction outside the optical axis as they pass through the concave cylindrical lens 65. Then, the light refracted by the concave cylindrical lens 65 is focused on the third focusing point C on the photodiode 10 side by the collimator lens 64. That is, the third focusing point C can be formed between the photodiode 10 and the detecting lens 8 by the concave cylindrical lens 65 unconnected to a second focusing point B disposed between the light source and the flow cell 7. Therefore, there is no need to deploy the light shielding plate 9 between the flow cell 7 and the detecting lens 8. Moreover, a detecting lens 8 having a short focal length may be used. The optical system can therefore be rendered far more compact.

Although described by way of examples of embodiments, the present invention is not limited to these embodiments.

The particles in the present invention are not particularly limited insofar as the particles can pass through a flow cell. Specific examples of particles include hemocytes such as erythrocytes, leukocytes, or platelets contained in blood, tangible materials such as bacteria, erythrocytes, leukocytes epidermal cells, or columnar epithelium contained in urine, and particles or powder such as toners and pigments and the like.

The flow cell used in the present invention is not particularly limited insofar as optical information can be obtained from particles passing through the interior of the flow cell. For example, transparent materials having a smooth surface are desirable. Specific examples include glass and the like.

The particle analyzer in the present invention is not particularly limited insofar as the analyzer detects optical information from particles passing through a flow cell using an optical flow cytometric method, and analyzes the morphological information of the particles based on the detected optical information. Examples of particle analyzers include blood analyzers, urine analyzers, toner analyzers, and pigment analyzers, among which blood analyzers and urine analyzers are desirable.

The light source used in the present invention is not particularly limited insofar as the light source is capable of emitting light. Examples of light sources include semiconductor lasers, argon lasers and the like.

The light from the particles in the present invention is not particularly limited insofar as such light is detectable by a photodetector. Examples of such detectable light include fluorescence, absorptivity, and light loss. Scattered light and fluorescent light are particularly desirable.

The irradiation optical system used in the present invention is not particularly limited insofar as the irradiation optical system is capable of forming a first focusing point that focuses light from a light source on particles passing through a flow cell, a second focusing point that focuses light from a light source at a position between a detecting lens and a photodetector. It is desirable that the irradiation optical system has at least one cylindrical lens. The first focusing point is desirably an elliptic spot that converges the light from a light source in a perpendicular direction (direction linear on the optical axis of the laser beam and parallel to the channel of the particles passing through the flow cell), and extends in a horizontal direction (direction linear on the optical axis of the laser beam, and linear to the channel of the particles passing through the flow cell). The second focusing point is desirably an elliptic spot converging in the horizontal direction, and extending in the perpendicular direction.

The photodetector used in the present invention is not particularly limited insofar as the photodetector is capable of photoelectric conversion of optical information to obtain light signals. Examples of such photodetectors include photodiodes, avalanche photodiodes, phototransistors, and photomultipliers. Photodiodes are desirable when detecting scattered light, and avalanche photodiodes and photomultipliers are desirable when detecting fluorescence.

The light shielding member used in the present invention is not particularly limited insofar as the light shielding member can block the transmission light passing through a flow cell without scattering the light from the light source by the particles. Examples include light shielding members provided with a wire-like light shielding part in the center of a circular aperture, and detecting lens with a black coated surface.

Various configurations of the above embodiments may be used in mutual combinations. When a plurality of configurations are included in a single embodiment, one or a plurality of configurations may be suitably selected from among the embodiments and used individually or in combination in the optical system of the present invention.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. An optical system for a particle analyzer, comprising:
   a light source for irradiating a particle passing through a flow cell with light;
   a photodetector for receiving light from the particle;
   a detecting lens, which is disposed between the flow cell and the photodetector, for directing the light from the particle toward the photodetector;
   a light shielding member, which is disposed between the detecting lens and the photodetector, wherein the light shielding member is configured for blocking direct light from the light source entering into the photodetector; and
   an irradiation optical system, which is disposed between the light source and the flow cell, for forming a first focus on the flow cell through which the particles pass, and forming a second focus on the light shielding members;
   wherein the irradiation optical system:
      forms the first focus that converges in a parallel direction relative to a direction of passage of the particle and extends in a perpendicular direction relative to the direction of passage of the particle;
      forms a third focus that converges in the perpendicular direction relative to the direction of passage of the particle and extends in the parallel direction relative to the direction of passage of the particle at a position between the flow cell and the light source; and
      forms the second focus by imaging the third focus with the detection lens.

2. The optical system for the particle analyzer of claim 1, wherein the irradiation optical system forms the first focus that converges in a parallel direction relative to a direction of passage of the particles and extends in a perpendicular direction relative to the direction of passage of the particles, and forms the second focus, that converges in the perpendicular direction relative to the direction of passage of the particles and extends in the parallel direction relative to the direction of passage of the particles, with the detecting lens.

3. The optical system for the particle analyzer of claim 1, wherein the irradiation optical system forms the first focus that converges in a parallel direction relative to a direction of passage of the particles and extends in a perpendicular direction relative to the direction of passage of the particles, and forms the third focus that converges in the perpendicular direction relative to the direction of passage of the particles and extends in the parallel direction relative to the direction of passage of the particles.

4. The optical system for the particle analyzer of claim 1, wherein the irradiation optical system has at least one cylindrical lens.

5. The optical system for the particle analyzer of claim 1, further comprising:
   a beam splitter disposed between the detecting lens and the light shielding member;
   a second photodetector for receiving one part of the light split by the beam splitter; and
   a second light shielding member disposed between the beam splitter and the second photodetector.

6. The optical system for the particle analyzer of claim 5, wherein the light shielding member has a first scattering angle range, and the second light shielding member has a second scattering angle range which is different than the first scattering angle range.

7. The optical system for the particle analyzer of claim 1, further comprising:
   a dichroic mirror disposed between the detecting lens and the light shielding member; and
   a fluorescence detector for receiving fluorescence split by the dichroic mirror.

8. The optical system for the particle analyzer of claim 1, wherein a second light shielding member is not disposed between the flow cell and the detecting lens.

9. A particle analyzer, comprising:
   a flow cell through which a particle pass;
   a light source for irradiating the particle passing through a flow cell with light;
   a photodetector for receiving light from the particle;
   a detecting lens, which is disposed between the flow cell and the photodetector, for directing the light from the particle toward the photodetector;
   a light shielding member, which is disposed between the detecting lens and the photodetector, wherein the light shielding member is configured for blocking direct light from the light source entering into the photodetector;
   an irradiation optical system, which is disposed between the light source and the flow cell, for forming a first focus on the flow cell through which the particles pass, and forming a second focus on the light shielding member; and
   an analyzing part for analyzing the particle based on the detection signals detected by the photodetector;
   wherein the irradiation optical system:
     forms the first focus that converges in a parallel direction relative to a direction of passage of the particle and extends in a perpendicular direction relative to the direction of passage of the particle;
     forms a third focus that converges in the perpendicular direction relative to the direction of passage of the particle and extends in the parallel direction relative to the direction of passage of the particle at a position between the flow cell and the light source; and
     forms the second focus by imaging the third focus with the detection lens.

10. The particle analyzer of claim 9, wherein the irradiation optical system forms the first focus that converges in a parallel direction relative to a direction of passage of the particles and extends in a perpendicular direction relative to the direction of passage of the particles, and forms the second focus, that converges in the perpendicular direction relative to the direction of passage of the particles and extends in the parallel direction relative to the direction of passage of the particles, with the detecting lens.

11. The particle analyzer of claim 9, wherein the irradiation optical system forms the first focus that converges in a parallel direction relative to a direction of passage of the particles and extends in a perpendicular direction relative to the direction of passage of the particles, and forms the third focus that converges in the perpendicular direction relative to the direction of passage of the particles and extends in the parallel direction relative to the direction of passage of the particles.

12. The particle analyzer of claim 9, wherein the irradiation optical system has at least one cylindrical lens.

13. The particle analyzer of claim 9, further comprising:
   a beam splitter disposed between the detecting lens and the light shielding member;
   a second photodetector for receiving one part of the light split by the beam splitter; and
   a second light shielding member disposed between the beam splitter and the second photodetector.

14. The particle analyzer of claim 13, wherein the light shielding member has a first scattering angle range, and the second light shielding member has a second scattering angle range which is different than the first scattering angle range.

15. The particle analyzer of claim 9, further comprising:
   a dichroic mirror disposed between the detecting lens and the light shielding member; and
   a fluorescence detector for receiving fluorescence split by the dichroic mirror.

16. A blood analyzer, comprising:
   a flow cell through which a blood cell pass;
   a light source for irradiating the blood cell passing through the flow cell with light;
   a photodetector for receiving light from the blood cells;
   a detecting lens, which is disposed between the flow cell and the photodetector, for directing the light from the blood cell toward the photodetector;
   a light shielding member, which is disposed between the detecting lens and the photodetector, wherein the light shielding member is configured for blocking direct light from the light source entering into the photodetector;
   an irradiation optical system which is disposed between the light source and the flow cell, for forming a first focus on the flow cell through which the blood cell pass, and forming a second focus on the light shielding member; and
   an analyzing part for analyzing the blood cell based on the detection signals detected by the photodetector;
   wherein the irradiation optical system:

forms the first focus that converges in a parallel direction relative to a direction of passage of the blood cell and extends in a perpendicular direction relative to the direction of passage of the blood cell;
forms a third focus that converges in the perpendicular direction relative to the direction of passage of the blood cell and extends in the parallel direction relative to the direction of passage of the blood cell at a position between the flow cell and the light source; and
forms the second focus by imaging the third focus with the detecting lens.

17. The blood analyzer of claim 16, wherein the irradiation optical system forms the first focus that converges in a parallel direction relative to a direction of passage of the blood cell and extends in a perpendicular direction relative to the direction of passage of the blood cell, and
forms the second focus, that converges in the perpendicular direction relative to the direction of passage of the blood cell and extends in the parallel direction relative to the direction of passage of the blood cell, with the detecting lens.

* * * * *

UNITED STATES PATENT AND TRADEMARK OFFICE
CERTIFICATE OF CORRECTION

PATENT NO. : 7,715,006 B2
APPLICATION NO. : 11/881323
DATED : May 11, 2010
INVENTOR(S) : Seiichiro Tabata It is certified that error appears in the above-identified patent and that said Letters Patent is hereby corrected as shown below:

In the Claims

In column 10, claim 1, line 54, after "light shielding" replace "members" with --member--.

In column 10, claim 1, line 67, after "with the" replace "detection" with --detecting--.

In column 12, claim 9, line 10, after "with the" replace "detection" with --detecting--.

Signed and Sealed this

Twenty-fourth Day of August, 2010

David J. Kappos
*Director of the United States Patent and Trademark Office*